United States Patent [19]

Libert et al.

[11] Patent Number: 4,992,535

[45] Date of Patent: Feb. 12, 1991

[54] METHODS OF MAKING NOVEL R AND S DIASTEREOMERS OF N[6]-[(2-HYDROXYPROPYL)ARYL]ADENOSINES

[75] Inventors: Valery Libert, Groot-Bijgaarden; Freddy Napora, Gembloux; Zoubida Bounkhala, Wavre, all of Belgium

[73] Assignee: G. D. Searle & Co., Chicago, Ill.

[21] Appl. No.: 262,859

[22] Filed: Oct. 26, 1988

[51] Int. Cl.[5] .................. A61K 31/70; C07H 19/67
[52] U.S. Cl. ................................ 536/26; 536/24; 514/45; 514/46
[58] Field of Search ............... 514/929, 46; 536/26

[56] References Cited

U.S. PATENT DOCUMENTS

| | | | |
|---|---|---|---|
| 3,502,649 | 3/1970 | Thiel et al. | 536/26 |
| 3,590,029 | 6/1971 | Koch et al. | 536/26 |
| 3,929,763 | 12/1975 | Fauland et al. | 536/26 |
| 4,388,308 | 6/1983 | Hamilton et al. | 536/26 |
| 4,837,207 | 6/1969 | Trivedi | 536/26 |

FOREIGN PATENT DOCUMENTS 55-22648 2/1980 Japan .
55-40658 3/1980 Japan .

*Primary Examiner*—Johnnie R. Brown
*Assistant Examiner*—Gary L. Kunz
*Attorney, Agent, or Firm*—Joy Ann Serauskas; Paul D. Matukaitis

[57] ABSTRACT

A method of making novel R and S diastereomers of an N[6]-[(2-hydroxypropyl)aryl] adenosine, which diastereomers exhibit fewer CNS side effects than the racemate, but with no decrease in cardiovascular activity.

3 Claims, No Drawings

METHODS OF MAKING NOVEL R AND S DIASTEREOMERS OF N⁶-[(2-HYDROXYPROPYL)ARYL]ADENOSINES

BACKGROUND OF THE INVENTION

The present invention provides for a novel method of manufacture, for the R and S diastereomers of an $N^6$-[(2-hydroxypropyl)aryl]adenosine, such compounds believed to be pharmacologically useful in the treatment of hypertension, congestive heart failure and angina in mammals. More specifically, the compounds made by the method of the present invention are orally active renin release inhibitor agents which, by blocking plasma renin activity, thereby block the production of angiotensin II, which is a powerful vasoconstrictor. Since renin is involved in the pathogenesis of hypertension, congestive heart failure and angina in mammals, it can be seen that the compounds made by the method of the present invention can be useful in the treatment of these pathological disease states. Also provided for are novel intermediates useful in the manufacture of the subject compounds.

Hypertension is a disease characterized by increased vascular resistance, increased arterial blood pressure, and, in some cases, increased plasma renin activity. Renin may be involved in the pathogenesis of hypertension even if its level is not elevated in the plasma.

The renin angiotensin system exists in every vertebrate class studied. The main source of renin is the kidney, from which it is secreted by the granular juxtaglomerular cells that lie in the walls of the afferent arterioles as they enter the glomeruli. These are endocrine cells in the sense that they discharge their secretory product, renin, directly into the renal arterial blood stream. Their peculiarity lies in the fact that renin is not itself a hormone but is an enzyme that catalyzes the formation of the active hormones, the angiotensins. Renin and the other components of the renin angiotensin system are also found at various extrarenal sites, including the brain Renin, which is a protease with high substrate specificity, is both the initiating and the rate limiting element in the production of the active peptide hormones. It releases the decapeptide angiotensin I by cleaving the peptide bond between residues #10 and #11 of its substrate, angiotensinogen. Angiotensinogens are glycoproteins, present in abundance in the plasma globulin fraction and synthesized by the liver. After renin acts on its substrate, angiotensinogen, to produce angiotensin I, angiotensin converting enzyme (ACE; Kininase II; Dipeptidyl Carboxypeptidase) catalyzes the conversion of angiotensin I into angiotensin II which is the classic vasoconstrictor agent with its powerful pressor effect.

U.S. Pat. No. 3,706,728 discloses that N(6) alkyl adenosine derivatives produce peripheral blood vessel dilating actions. It has been further taught that N(6) [2 hydroxy-3-(1 naphthyloxy)propyl]-adenosine (I) binds to the adenosine Al receptor in the granular juxtaglomerular cells of the kidney to inhibit release of renin into the plasma, ultimately resulting in a reduction in circulating angiotensin II, thus reducing arterial blood pressure and heart rate in hypertensive models (Federation Proceedings 44:879 & 1643, 1985). Thus, this compound has an excellent profile for the treatment of hypertension and congestive heart failure and may also be useful in the treatment of angina.

One of the disadvantages of other adenosine analogs is that they produce sedation and generalized central nervous system depression. Thus, there is a need in this art for a renin inhibiting compound which has a decreased incidence of such side effects. It is an object of the present invention to produce a compound which will effectively inhibit the production of renin, and which will display a lowered incidence of the side effects of sedation and central nervous system depression.

SUMMARY OF THE INVENTION

Compound I is represented by the formula:

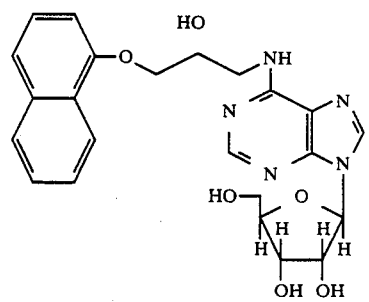

This compound is disclosed in U.S. Pat. No. 4,388,308. The '308 patent did not characterize this compound as a racemate or teach that there were desirable isomeric forms, nor suggest any method of resolution of the racemate. Compound I was subsequently resolved into two isomeric forms at the number two carbon of the propyl moiety. The diastereomers displayed different solubilities and melting point. Further investigation revealed that although they had a similar pharmacologic profile, the R diastereomer (II):

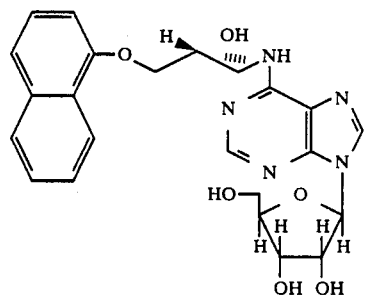

had less central nervous system toxicity than the S diastereomer (III):

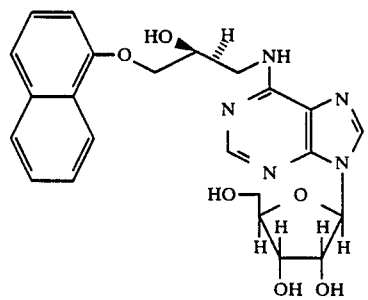

as well as having less central nervous system toxicity than the racemic mixture of the two (I). This property of the R diastereomer was unexpected because the diastereomers and the racemic mixture thereof appeared to be otherwise identical pharmacologically. The novel chiral synthesis of the R diastereomer of compound I and of the S diastereomer and their respective pharmaceutically acceptable salts, produced a compound useful in the treatment of hypertension, congestive heart failure and angina. Also provided for in this invention is a method for making the pharmaceutically acceptable salts of the diastereomer.

DETAILED DESCRIPTION OF THE INVENTION

As used herein the expression "hypertension" is defined as a persistently high arterial blood pressure which may have either no known underlying cause (primary, idiopathic or essential hypertension) or which may have a known cause (secondary hypertension) due to or associated with a variety of primary diseases, such as renal disorders, disorders of the central nervous system, endocrine diseases and vascular diseases.

The term "congestive heart failure" is defined to mean a syndrome in a mammal due to heart disease and characterized by breathlessness and abnormal sodium and water retention, resulting in edema and congestion, which congestion may occur in the lungs or the peripheral circulation, or in both, depending on whether the heart failure is right-sided, left sided or general. The term "angina" is defined as spasmodic, choking, or suffocative pain, and especially as denoting angina pectoris which is a paroxysmal thoracic pain due, most often, to anoxia of the myocardium.

The term "pharmaceutically acceptable salts" refers to non toxic salts of the compounds of this invention which are generally prepared by reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate, clavulanate and the like salts.

The method of the present invention is useful in synthesizing diastereomers of $N^6$-[(2-hydroxypropyl)aryl]adenosines. Most especially preferred compounds made by the invention are those which are namely N-[2R-hydroxy-3-(1-naphthalenyloxy)propyl]-adenosine, and the pharmaceutically acceptable salts thereof, and which is of the formula:

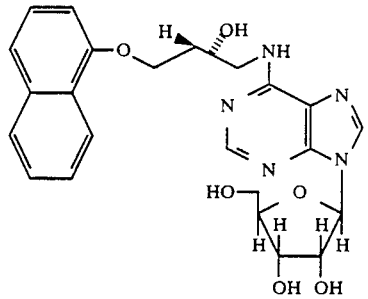

and the compound namely N-[2S-hydroxy-3[1-naphthalenyloxy) propyl]-adenosine, and the pharmaceutically acceptable salts thereof, and which is of the formula:

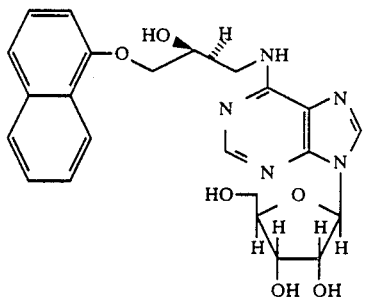

Compounds of the invention can be prepared readily according to one of the following reaction schemes or modifications thereof using readily available starting materials, reagents and conventional synthesis procedures. In these reactions, it is also possible to make use of variants which are in themselves known, but are not mentioned here in greater detail.

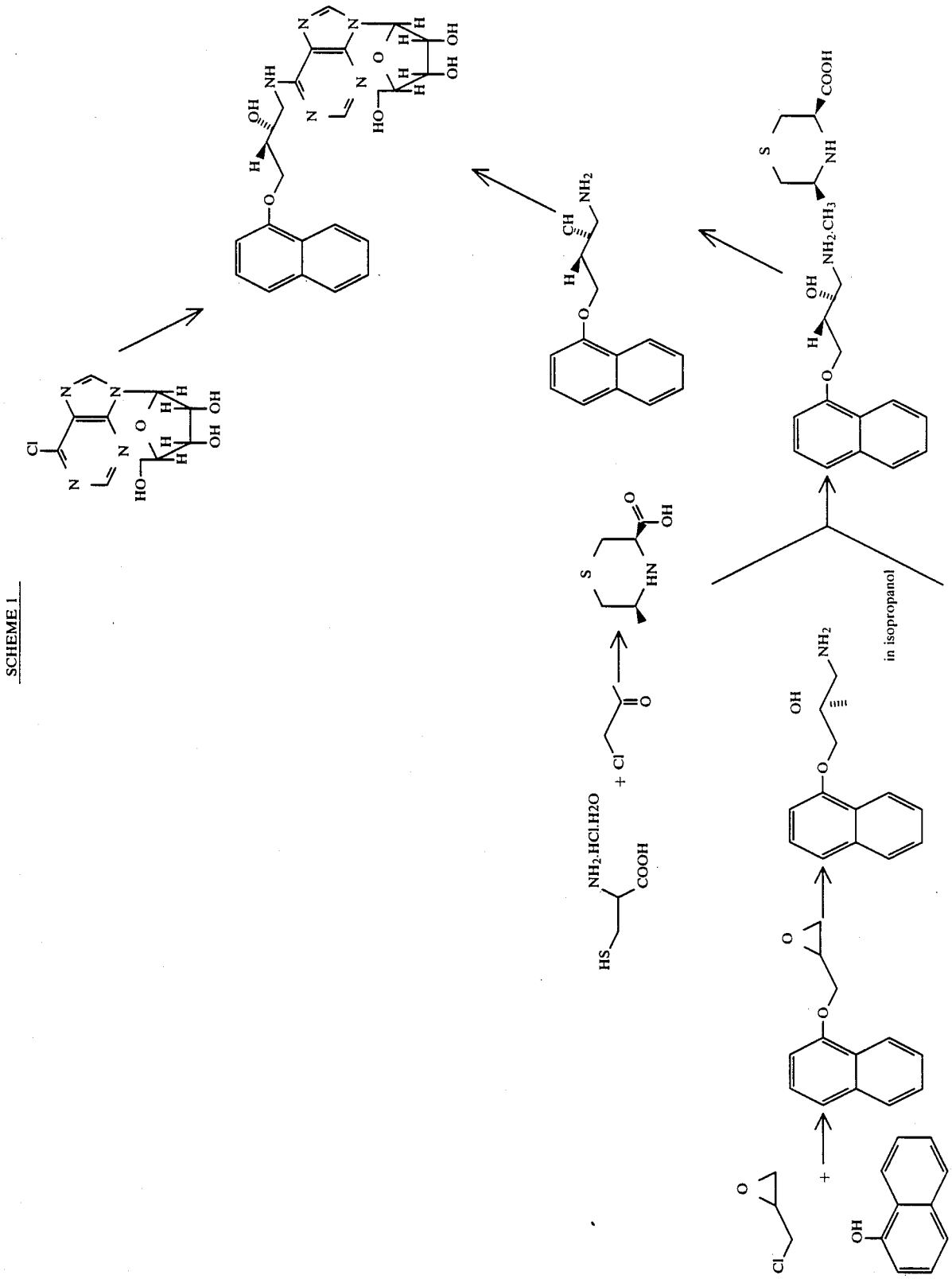
SCHEME 1

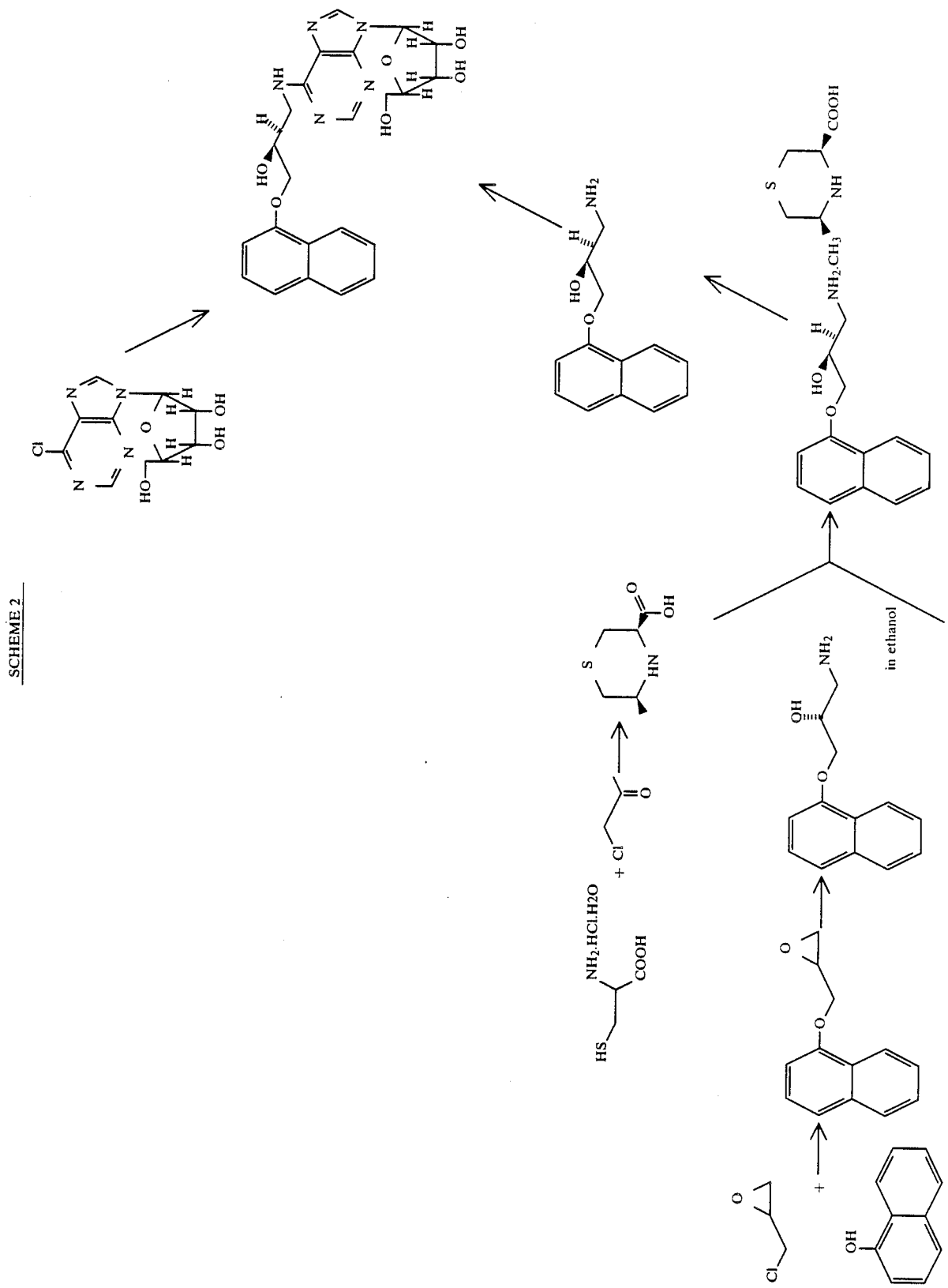

In the aforementioned reaction schemes, several novel intermediate compounds likewise are part of the present invention. They are namely 1-amino-3-(1-naphthalenyloxy)-2S-propanol, which is of the structure

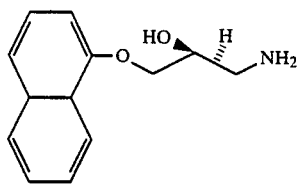

1-amino-3-(1 naphthalenyloxy)-2R-propanol, which is of the structure

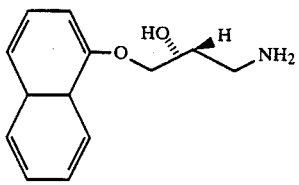

The compounds produced by the present invention can be administered in such oral dosage forms as tablets, capsules, pills, powders, granules, elixirs, tinctures, suspensions, syrups, emulsions and suspensions. Likewise, they may also be administered in intravenous, intraperitoneal, subcutaneous or intramuscular form, all using forms known to those of ordinary skill in the pharmaceutical arts. In general, the preferred form of administration is oral. An effective but non toxic amount of the compounds are employed in the treatment of hypertension, angina or congestive heart failure. The dosage regimen utilizing the compounds produced by the present invention is selected in accordance with a variety of factors including the type, species, age, weight, sex and medical condition of the patients; with the severity of the condition to be treated, the route of administration, the renal and hepatic function of the patient, the route of administration and the particular compound employed or salt thereof. An ordinarily skilled veterinarian or physician can readily determine and prescribe the effective amount of the drug required to prevent, treat or arrest the progress of the condition.

Oral dosages of the compounds produced by the present invention, when used for the indicated cardiovascular effects, will range between about 0.1 mg/kg/day to about 1000 mg/kg/day and preferably 1.0 to 100 mg/kg/day. Advantageously, the compounds produced by the present invention may be administered in a single daily dose or the total daily dosage may be administered in divided doses of 2, 3 or 4 times daily. In the pharmaceutical compositions and methods of utilizing the compounds made by the present invention, the foregoing compounds described in detail above will form the active ingredient and will typically be administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of tablets or capsules, the active drug component may be combined with an oral non toxic pharmaceutically acceptable inert carrier such as lactose, starch, sucrose, glucose, methylcellulose, magnesium stearate, dicalcium phosphate, calcium sulfate, mannitol, sorbitol and the like; for oral administration in liquid form, the active drug components may be combined with any oral non-toxic pharmaceutically acceptable inert carrier such as ethanol, glycerol, water, and the like. Moreover, when desired or necessary, suitable binders, lubricants, disintegrating agents and coloring agents can also be incorporated in the mixture. Suitable binders include starch, gelatin, natural sugars such as qlucose or beta lactose, corn sweeteners, natural and synthetic gum such as acacia, tragacanth or sodium alginate, carboxymethylcellulose, polyethylene glycol and waxes. Lubricants for use in these dosage forms include boric acid, sodium benzoate, sodium acetate, sodium chloride and the like. Disintegrators include, without limitation, starch, methylcellulose, agar, bentonite, xanthan gum and the like.

The compounds produced by this invention may also be administered by intravenous route in doses ranging from 0.01 to 10 mg/kg/day.

The compounds produced by this invention exhibit renin release inhibiting activity useful in the treatment of hypertension, congestive heart failure and angina. The test procedures employed to measure this activity of the compounds produced by the present invention are described below.

The effects of compounds I and II were tested intravenously or intragastrically in conscious spontaneously hypertensive rats (SHR). The rats were anesthetized with ether and the left carotid artery and right jugular vein were cannulated with polyethylene tubing. The rats were allowed three to five hours recovery from anesthesia for the I.V. studies and 12 to 18 hours for the oral studies. Mean arterial pressure (MAP, in mm/Hg) and heart rate (HR, beats/min.) were measured from the artery; intravenous administration of compounds was performed by injection into the vein. Oral administration was performed by gastric intubation. Compounds were dissolved in DMSO for I.V. studies and injected in volumes of 100 ml/kg or less (N=5 per compound). Doses were 3 to 1,000 mg/kg. Compounds were dissolved in polyethylene glycol for oral administration and injected in volumes of 1 ml/kg at dose of 20 mg/kg/day for three days (N=3 to 6 per compound).

The resting MAP and HR for the SHR ranged between 160–200 mm Hg and 330/350 b/min., respectively. The effects of the compounds on MAP and HR are shown in Table I.

TABLE I

| | Effects of compounds I and II, and III on MAP and HR in SHR | | | |
|---|---|---|---|---|
| | IV DOSE (μg/kg) TO | | | |
| | DECREASE MAP by | DECREASE HR by | MAXIMUM DECREASE AT 20 MG/KG ig | |
| COMPOUND | 40 mmHg | 100 b/min | MAP (mmHg) | HR (b/min) |
| I | 52 ± 1.3 | 37 ± 1.3 | 50 ± 13 | 214 ± 14 |
| II | 47 ± 1.2 | 36 ± 1.2 | 62 ± 7 | 202 ± 24 |

TABLE I-continued

Effects of compounds I and II, and III on MAP and HR in SHR

| COMPOUND | IV DOSE (µg/kg) TO | | MAXIMUM DECREASE AT 20 MG/KG ig | |
|---|---|---|---|---|
| | DECREASE MAP by 40 mmHg | DECREASE HR by 100 b/min | MAP (mmHg) | HR (b/min) |
| III | 33 ± 1.2 | 31 ± 1.4 | 50 ± 14 | 177 ± 19 |

MAP = mean arterial pressure;
HR = heart rate;
SHR = spontaneously hypertensive rat The intravenous doses required to decrease MAP by 40 mm Hg ranged between 33 and 52 mg/kg and were not significantly different among the compounds. The doses required to decrease HR by 100 b/min. ranged between 31 and 37 mg/kg and also were not significantly different among the compounds. Table I also shows the effects of the compounds on day 2 of oral administration which are representative of the results from 3 days of testing. All three compound lowered MAP and HR to the same extent with a similar duration of action after oral administration. Thus, the effects of the three compounds on MAP and HR were indistinguishable both by I.V. and oral administration.

The inhibition of the release of renin reduces the amount of circulating renin and the activity of plasma renin. The reduction in plasma renin activity (PRA) is associated with a reduction in circulating angiotensin II. Angiotensin II is a potent vasoconstrictor and is responsible for elevated vascular resistance and high blood pressure in hypertension. Inhibition of renin release is, therefore, expected to be useful in the treatment of hypertension by reducing the amount of circulating angiotensin II. Likewise, inhibition of renin release may be expected to be useful in the treatment of angina and congestive heart failure by inducing vasodilation to reduce the afterload of the myocardium. Also, inhibition of renin release may further be expected to be useful in the treatment of angina, since indirectly inhibiting the formation of angiotensin will prevent angiotensin's direct action on the membrane of atrial and ventricular muscle (angiotensin prolongs the plateau phase of the action potential, increasing inward calcium current and force of contraction thus increasing the work of the heart.) Furthermore, inhibition of renin may be expected to be useful in congestive heart failure, since the essential hypertension caused by elevated renin levels is itself one of the cause of the decreased cardiac output that initiates the vicious cycle of the congestive heart failure syndrome.

The compounds produced by the present invention inhibit the release of renin by activation of adenosine A1 receptors in the granular juxtaglomerular cells of the kidney. The binding potency of compound I, II and III to the adenosine A1 receptor was measured according to the method of Schwabe, U. et al., Naunyn Schmeid. Arch. Pharmacol. 321:84, 1982. Crude plasma membranes were prepared and varying concentrations of compounds I, II or III were added to the membrane preparation in the presence of $^{125}$-N-p hydroxyphenyl isopropyladenosine (HPIA). The affinity of the compounds for the adenosine A1 receptor was estimated from the concentrations necessary to inhibit the binding of HPIA by 50% (IC50). The results of these studies are shown in Table II.

TABLE II

| BINDING POTENCY (IC50) OF COMPOUNDS I AND II FOR THE ADENOSINE A1 RECEPTOR | |
|---|---|
| COMPOUND | IC50 ($10^{-9}$M) |
| I | 1.2 |
| II | 1.2 |
| III | 1.2 |

The IC50's of the compounds were identical, indicating that they all had the same relative affinity for the adenosine A1 receptor.

Adenosine A1 receptor stimulation will inhibit the release of renin from the kidney. A stimulus for the release of renin is renal ischemia. The ability of the compounds of the present invention to prevent an increase in PRA following renal ischemia was tested in rats with both renal arteries ligated. Sprague Dawley rats were anesthetized with ether and the renal arteries were ligated. Three to five hours after anesthesia, arterial blood was sampled and compounds I, II or III were administered in polyethylene glycol at 1 mg/kg I.V. At 30 and 60 minutes after administration, arterial blood was sampled for PRA measurement by the method of Sealy, J. E. et al., Cardiovasc. Med. 2:1079, 1977. The results are presented in Table III.

TABLE III

| EFFECTS OF COMPOUNDS I, II AND III ON PRA AT 30 AND 60 MINUTES AFTER DOSING IN THE BILATERAL RENAL ARTERY LIGATED RAT | | |
|---|---|---|
| | CHANGE IN PRA (ngAI/ml/hr) | |
| COMPOUND | 30 minutes | 60 minutes |
| VEHICLE | 4.5 ± 1.1* | 12 ± 2.7* |
| I | −2.9 ± 5.0 | −9.4 ± 7.4+ |
| II | −11.7 ± 3.5+,*, # | −13.8 ± 4.9+,* |
| III | −6.6 ± 4.0+ | −6.3 ± 3.9+ |

* = different from zero, p <.05;  + = different from vehicle, p <.05; # = different from I, p <.05.

With vehicle treatment there were increases in PRA above pre treatment levels at 30 and 60 minutes. These increases were prevented to the same extent by compounds I, II and III. Thus, these compounds appeared equieffective in inhibiting the release of renin.

Adenosine analogs tend to produce sedation and central nervous system depression which have prevented their therapeutic utility. The compounds of the invention, at doses which lower arterial pressure in the SHR, show no evidence of CNS depression. The ataxia produced by compounds of the present invention was measured in mice by injecting the compounds IP at doses of 32, 56, or 75 mg/kg in an aqueous suspension, n=7 per dose. The mice had previously been trained to remain on a rotating rod. After dosing, the percent of mice unable to remain on the rotating rod was determined. Analysis of the results indicated that there were not significant differences among the three doses used, so the results were pooled for the three doses (average =54% 12 mg/kg). The mice were also observed at various time intervals for behavioral signs of toxicity.

Table IV shows the results of the rotating rod studies. Compounds II and III produced less ataxia at 0.5 or 3 hours as compared to compound I.

TABLE IV

ATAXIC EFFECTS OF COMPOUNDS I, II AND III (54 ± 12 mg/kg ip) IN MICE

| COMPOUND | PERCENT ATAXIC | |
|---|---|---|
| | 0.5 HOUR | 3 HOUR |
| I | 33 ± 10 | 95 ± 5 |
| II | 14 ± 8* | 48 ± 21* |
| III | 14 ± 0* | 57 ± 8* |

* = Significantly different from compound I, $p < .05$

Thus, compounds II and III produced less motor toxicity than compound I. Table V shows the results on behavioral changes at 75 mg/kg at various times after administration.

TABLE V

BEHAVORIAL TOXICITY AT VARIOUS TIMES AFTER 75 MG/KG IP IN MICE

| TIME (HR) | MOTOR DEPRESSION | PTOSIS | RESPIRATORY DEPRESSION | FLACCIDITY | LOSS OF RIGHTING REFLEX |
|---|---|---|---|---|---|
| CMPD I | | | | | |
| 0.5 | + | + | + | | |
| 3 | + | + | + | | |
| 18-20 | + | + | + | + | + |
| 24 | | | | +* | |
| CMPD II | | | | | |
| 0.5 | + | + | + | | |
| 3 | + | + | + | | |
| 18-20 | + | + | + | + | |
| 24 | +# | +# | # | | |
| CMPD III | | | | | |
| 0.5 | + | + | + | | |
| 3 | + | + | + | | |
| 18-20 | | | | | |
| 24 | | | | | |

+ = toxic symptom observed; * = 2/7; # = 5/7

All three compounds produced similar toxicity at 0.5 hours, which included motor depression, ptosis, and respiratory depression. At 3 hours, compound I also produced flaccidity and loss of writhing reflex. AT 18-20 hours, compounds I and II were still producing several of the toxic symptoms but no toxicity was observed with compound III. At 24 hours, compound II was still producing toxic symptoms. These results show that compound III is substantially less toxic than compounds I and II because its toxic effects were not sustained as with compounds I and II. This result is totally unexpected because compounds II and III are diastereomers and compound I is an approximate 1:1 racemic mixture of II and III.

The results of the biological testing demonstrate that compounds I, II and III have a similar pharmacologic profile but that compound III is unexpectedly less CNS toxic than compound II with regard to behavioral toxicity, which itself is unexpectedly less toxic than compound I with regard to ataxia. Thus, compounds II or III may be administered to mammals for the treatment of hypertension and other cardiovascular diseases such as congestive heart failure and angina pectoris in doses that produce less central nervous system toxicity than compound I.

The following non limiting examples further illustrate details for the present invention. Those skilled in the art will readily understand that known variations of the conditions and processes of the following preparative procedures can be used to prepare these compounds. All temperatures are degrees Celsius unless otherwise noted. Melting points are not corrected. Unless otherwise noted, I.R. and NMR spectra were consistent with the assigned structure.

EXAMPLE 1

[(1-naphthalenyloxy)methyl]oxirane

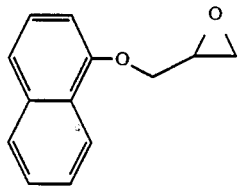

28 9 Kg (309 moles) of chloromethyloxirane, 39 L of a 33% w/v solution of sodium hydroxide in water, 32 L of toluene and 0.9 Kg of tetrabutylammonium hydrogen sulfate are poured in a stainless steel reactor. 9 Kg (61.B moles) of 1-naphthol are added under efficient agitation in 45 min. minimum. The temperature is kept under 25° C. The agitation is maintained until reaction completion (about 20 hours). The aqueous layer is discarded and the organic phase extracted by 18 L of water and then with 18 L of an aqueous sodium chloride solution (5.5% w/v). The organic layer is concentrated under reduced pressure to yield 11.6 Kg of crude product. The crude product is used in the next reaction step.

Yield: 92.8% from 1-naphthol.

$^1$H NMR (CDCL$_3$):$\delta$2.74(1H,dd,13a),$\delta$2.87(1H,dd,13b), $\delta$3.39(1H,m,12)$\delta$3.98(1H,dd,11a),$\delta$4.28(1H,dd,11b),$\delta$6.72(1H,dd,2),$\delta$17-7.48(4H,m,3,4,7,8), $\delta$7.75(1H,dd,6),$\delta$8.28(1H,dd,9).

$^{13}$C NMR (CDCL$_3$):$\delta$44.6(t,13),$\delta$50.2(d,12),$\delta$68.9 (t,11),$\delta$105.0(d,2),$\delta$120.8(d,4),$\delta$122.0(d,9), $\delta$125.3(d,8),$\delta$125.6(s,10),$\delta$125.8(d,7),$\delta$126.5 (d,3),$\delta$127.5(d,5)$\delta$134.5(s,5)$\delta$154.2(s,1).

EXAMPLE 2

(±)1-amino-3-(1-naphthalenyloxy)-propanol

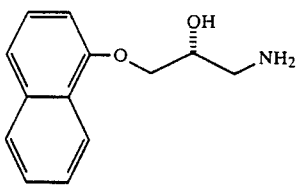

116 L Of methanol are cooled to about 10° C. and saturated with gaseous ammonia (11.2 Kg), then 1.2 Kg of gaseous ammonia are additionally condensed at room temperature. 11.34 Kg of the product of Example 1 are dissolved in 6 L of methanol and added to the ammonia solution (T≦30° C.). After completion of addition, the reaction mixture is once again saturated with gaseous ammonia (2.8 Kg) at the same temperature. The reaction mixture is stirred overnight. The excess of ammonia is eliminated under reduced pressure (P=350 mbar at about 30° C.). The methanol is distilled under reduced pressure (P=20 mbar at about 40° C.). The residue is dissolved in 12 L of dichloromethane, then 39 L of water and 11 L of acetic acid are added. The mixture is stirred for about 30 min. and decanted. The aqueous layer is extracted twice with 6 L of dichloromethane. 33 L of toluene and 18 L of aqueous sodium hydroxide solution (30% w/v) are added to the aqueous layer. The reaction mixture is heated to T<70° C. and stirring is continued for about 1 hour. At this temperature the aqueous layer discarded and the organic layer re extracted twice with hot water. The remaining organic phase is concentrated under reduced pressure and the residue dissolved in 16 L of ethyl acetate at the reflux temperature. The product is crystallized (0° C≦T≦5° C.), filtered, washed with ethyl acetate and dried under reduced pressure at about 50° C. to afford 4.86 Kg of crude product.

Yield: 39.6%.

Purification:

The crude product (4.86 Kg) is dissolved in 14 L of ethyl acetate at the reflux. The solution is cooled to room temperature to allow crystallization. The solid is filtered, washed with ethyl acetate and dried under reduced pressure at about 50° C. to afford 4.08 Kg of purified product.

DSC(MP)=105.9° C.

Yield: 83.9%.

EXAMPLE 3

Cis-5-methyl-3R-thiomorpholine carboxylic acid

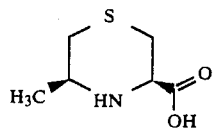

0.54 L (6.83 moles) of methylchloroacetate is slowly added to a solution of 1.0 Kg (5.69 moles) of L-cysteine in 2.5 L of deionised water. During the addition the temperature of the reaction is maintained between 20° C.<T<45° C. After completion of the addition, the reaction mixture is stirred for about 2 hours at room temperature. The excess of methylchloroacetate is extracted with dichloromethane. 1.24 L (10.19 moles) of aqueous sodium hydroxide solution (33% w/v) are added to the aqueous layer (pH=1.6, T<25° C.). After completion of the addition, a solution of 0.12 Kg (3.17 moles) of sodium borohydride and 0.8 g of sodium hydroxide (33% w/v) in 0.37 L of water is dropped (T≦36° C., pH=5,6). The mixture is further stirred for minimum 1 hour at room temperature and concentrated under reduced pressure. The residue is triturated with a mixture of 0.7 L of acetic acid and 4.9 L of dichloromethane. The solid is filtered and rinsed with a mixture of 0.1 L of acetic acid and 0.9 L of dichloromethane. The dichloromethane is evaporated from the filtrate. 0.5 L of water and 1 L of hydrochloric acid (12N) are added to the residue. The suspension is agitated during about 15 min. All solvents are evaporated under reduced pressure and the residue suspended in 3 L of hot isopropanol for about 1 hour. The suspension is cooled to room temperature and stirred for about 1 hour. The solid is filtered and washed with isopropanol. A second crop is obtained from the residue of evaporation of the filtrate by applying the same treatment with a smaller quantity of isopropanol (typically about 1.5 L). The two crops are pooled and dried under reduced pressure at about 75° C., yielding 0.795 Kg of crude salt.

The crude salt is purified by ion exchange chromatography. 0.793 Kg of salt dissolved in 20 L of water is applied on an IR-120 (H+) column. The column is eluted first with deionised water until the pH of the eluent reaches pH 5 to 6. This fraction is discarded. The column is then eluted with about 10 L of 1.2N ammonium hydroxide and with 10 L of water. These fractions of elution are pooled and evaporated under reduced pressure. The residue is suspended in 4 L of acetone at room temperature for about 1 hour. The solid is filtered, washed with 1 L of acetone and dried under reduced pressure at about 75° C. to afford 558 of product.

Yield: 60.8%.

$^1$H NMR (D20):δ1.43(3H,d,8),δ2.82(2H,m,6),δ2.92 (1H,dd,2axial)δ3.1(1H,dd,2equatorial),δ3.52 (1H,tq,5)δ3.82(1H,dd,3).

EXAMPLE 4

1-amino-3-(1-naphthalenyloxy-2R-propanol

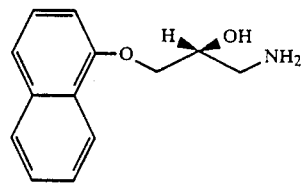

2.70 Kg (12.43 moles) of the product of Example 2 are added to 103 L of isopropanol. The suspension is heated between 40° C. and 55° C. under stirring until dissolution. The reaction mixture is cooled to room temperature and 1.39 Kg (8.63 moles) of the product of Example 3 are added. The suspension is heated to reflux for about 1 hour and then cooled to room temperature. The stirring is continued for about 1 hour. The solid is filtered and washed with 5 L of isopropanol to yield 2.685 Kg of a salt. (Yield: 57%)

The filtrate is evaporated under vacuum (about 50° C.) and the residual isopropanol eliminated by distillation after addition of 20 L of water. 0.9 L of an aqueous solution of sodium hydroxide (30% w/v) is added to reach a pH=9 to 10. The resulting suspension is stirred for about 30 min. 34 L of ethyl acetate are added and the mixture is stirred until dissolution. The aqueous layer is decanted and the organic phase further extracted with deionised water. The organic phase is concentrated to dryness under reduced pressure. The residue is recrystallized in ethyl acetate. The crystals are all filtered, rinsed with ethyl acetate and dried under reduced pressure at about 50° C. to afford 0.925 Kg of product.

$[\alpha]_{365}^{23°}$ C.=+78.5°(c=0.6% in acetic acid);ee=99%;DSC(MP)=120,4° C.

Yield: 34.3%.

$^1$H NMR (DMSO-d6);2.70(1H,dd,13a),2.84(1H,dd,13b),3.90 (1H,m,12),δ4.07(1H,dd,11a),δ4.13(1H,dd,11b), δ6.97(1H,dd,2),δ7.37–7.55(4H,m,3,4,7,8),δ7.86 (1H,dd,6),δ8.25(1H,dd,9).

EXAMPLE 5

1-amino-3-(1-napthalenyloxy)-2S-propanol

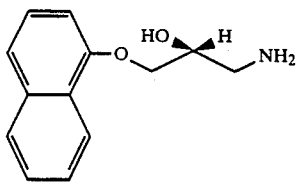

31.57 g (0.145 mole) of the product of Example 2, 26.48 g (0.148 mole) of the product of Example 3 are added to 1.3 L of ethanol. The suspension is heated to reflux for about 1 hour and then cooled to room temperature for about 2 hours. The crystals are filtered, washed with 130 mL of ethanol and dried under reduced pressure to yield 29.56 g of salt. $[\alpha]_{365}^{24°}$ C.=−76°(c=0.6 in methanol).

The salt (29 g) is suspended in 325 mL of ethanol. The suspension is heated to reflux for about 1 hour and agited for 1 hour at room temperature. The solid is filtered, rinsed with 35 mL of ethanol and dried under reduced pressure yielding 26.8 g of purified salt.

$[\alpha]_{365}^{24°}$ C.=−76.33°(c=0.6 in methanol).

The purified salt (26 g) is suspended for about 30 min. in a mixture of 260 mL of water, 38 mL of 2N sodium hydroxide and 13 mL of methanol. 260 mL of ethyl acetate are added. The mixture is stirred until dissolution of the solids. The aqueous layer is decanted. The organic solvent is evaporated under reduced pressure and the residue is dried under vacuum to afford 13.3 g of product. $[\alpha]_{365}^{24°}$ C.=−71.33°(c=0.6 in acetic acid);ee=90%;DSC(MP)=118.2° C. Yield: 44%.

EXAMPLE 6

9-(2,3,5-tri-O-acetyl-β-D-ribofuranosyl)-9H-purin-6-ol

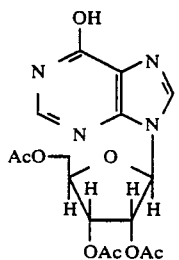

A suspension of 0.367 Kg (1.36 moles) of Inosine, 0.52 Kg (5.51 moles) of acetic anhydride and 5.6 g (0.068 mole) of sodium acetate is heated between 90° C. and 140° C. for about 4 hours. At the end of the reaction, the solids are dissolved. The reaction mixture is then cooled to about 45° C. and 0.75 L of ethyl acetate are added. The resulting suspension is stirred for about 1 hour at room temperature. The solid is filtered, washed with ethyl acetate and dried under reduced pressure at about 60° C. to afford 0.487 Kg of crude product. The crude product is used in the next reaction.

Yield: 91%. $^1$H NMR (DMSO-d6);δ2.03–2.12(9-H,OAC),δ4.25(1H,m,4'), δ4.39(2H,m,5'),δ5.55(1H,dd,3'),δ5.91 (1H,dd,2'),δ6.20(1H,d,1'),δ8.12(1H,s,8),δ8.33 (1H,s,2). $^{13}$C NMR (DMSO-d6);δ20.10–20.27–20.41(-q,OCH3),δ62.7 (t,5'),δ69.8(d,3'),δ72.1(d,2'),δ79.4(d,4'), δ85.5(d,1'),δ124.7(s,5),δ139.2(d,8),δ146.2 (d,2),δ147.9(s,4),δ156.4(s,6),δ169.2–169.4–169.9(s,-C=O).

EXAMPLE 7

6-chloro-9-(2,3,5-tri-O-acetyl-β-D-ribofuranosyl)-9H-purine

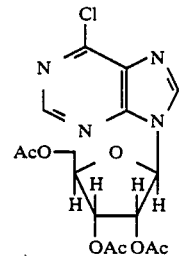

A Solution of 151 mL (1.97 moles) of dimethylformamide in 3.1 L of dichloromethane is cooled down between −5° C. and 0° C. The solution is stirred and 172 mL (1.97 moles) of oxalyl choride are added whilst the temperature of the reaction mixture is maintained below 0° C. After the addition is complete, the temperature is increased to 20° C.–25° C. for about 3g min. 485 g (1.23 moles) of the product of Example 6 are added to the suspension and the reaction mixture is heated to reflux for about 9 hours. The reaction mixture is then cooled and stirred for about 12 hours at room temperature. The solid is filtered and washed with 400mL of dichloromethane. The filtrate and the washes are combined and cooled to about 5° C. and extracted (until neutralization) with an aqueous sodium bicarbonate solution (1.5N). The aqueous layer is extracted with dichloromethane. The combined organic layers are washed with water. The organic layer is concentrated under reduced pressure to afford 536 g of crude product. The crude product is used in the next reaction step.

Yield: Quantitative (weight yield: 536 g).

$^1$H NMR (CDCL3):δ2.10–2.17(9H,OAC),δ4.35–4.53 (3H,m,5'+4'),δ5.67(1H,dd,3'),δ5.98(1H,dd,2'), δ6.28(1H,d,1')δ,8.40(1H,s,8),δ8.78(1H,s,2).

$^{13}$C NMR (CDCL3):δ20.38–20.53–20.73(-q,OCH3),δ62.9 (t,5'),δ70.4(d,3'),δ73.1(d,2'),δ80.5(d,4'), δ86.9(d,1'),δ132.3(s,5)δ,143.9(d,8),δ151.3 (s,4),δ151.4(s,6)δ152.2(d,2),δ169.4–169.6–170.3(s,-C=O).

EXAMPLE 8

6-chloro-9-β-D-ribofuranosyl-9H-purine

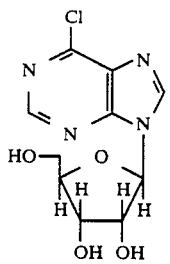

532 g of the product of Example 7 are dissolved in 2.43 L of dry methanol. The solution is cooled at about −11° C. and 13.2 g of sodium methoxide are added under stirring. When the addition is complete the stirring is continued for minimum 1 hour. The temperature is raised to 20° C.-25° C. for minimum 2 hours. The precipitate is filtered and rinsed with methanol to afford 304.6 g of crude product.

Yield: 86.4%.

Purification:

297.6 g of crude product is suspended in 1.65 L of a methanol/water 10/1 mixture and heated to reflux for about 4 hours. The reaction mixture is cooled to room temperature for about 1 hour. The solid is filtered, washed with methanol and dried under reduced pressure at about 55° C. to afford 248 g of purified product.

$[\alpha]_{365}^{24°}$ C. = −135.7°(c=1 in DMF);MP=169° C.

Yield: 83.4%.

$^1$H NMR (DMSO-d6):δ3.62(1H,dd,5′a),δ3.73(1H,dd,5′b), δ4.01(1H,dt,4′)δ4.22(1H,dd,3′),δ4.62 (1H,dd,2′),δ5.13(1H,t,OH-5′),δ5.29(1H,d,OH-2′), δ5.61(1H,d,OH-3′),δ6.07(1H,d,1′),δ8.83 (1H,s,8),δ8.97(1H,s,2).

$^{13}$C NMR (DMSO-d6):δ61.1(t,5′),δ70.2(d,3′),δ74.1 (d,2′),δ85.9(d,4′),δ88.3(d,1′),δ131.6(s,5), 145.9(d,8),δ149.5(s,4)δ151.8(s,6),δ151.9 (d,2).

EXAMPLE 9

N⁶-[2R-hydroxy-3-(1-naphthalenyloxy)propyl adenosine

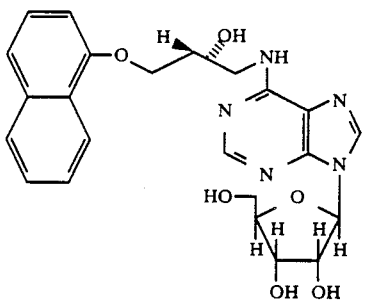

577 g (2.65 moles) of the product of Example 4 are dissolved in 15.4 L of methanol. 390 mL (2.79 moles) of triethylamine and 725 g (2.53 moles) of the product of Example 8 are added at room temperature. The reaction mixture is heated to reflux for about 7 hours and then cooled to 40° C.<T<60° C. 31 L of water are added. The reaction mixture is cooled to 15° C.<T<25° C. for minimum 2 hours. The crystalline product is filtered, washed with 5 L of a mixture of methanol and water (1:2) and dried under reduced pressure (about 70° C.-80° C.) to afford 1 Kg of crude product.

Yield: 84.6%.

First purification:

The crude product (0.5 kg) is dissolved in 4.735 L of a mixture of methanol and water (95/5) a reflux temperature. The solution is cooled to 15° C.<T<25° C. and stirred at that temperature for minimum 2 hours. The solid is filtered, washed with a mixture of methanol and water (95/5) and dried under reduced pressure at about 75° C. to afford 424 g of product.

Yield: 84.8%.

Second purification:

The suspension of 836.8 g of product in 8.79 L of a mixture of ethanol and water (20:1) is heated to reflux for about 8 hours. The mixture is cooled to 15° C.<T<25° C. and stirring is continued for minimum 2 hours. The solid is filtered, washed with water and dried under reduced pressure at about 75° C. to afford 825.8 g of purified product.

$[\alpha]_{579}^{25°}$ C. = −44.8°(c=0.5 in DMF);DSC(MP)=163.2° C.

Yield: 98.7%.

$^1$H NMR (CD3OD):δ3.82(1H,dd,5′b),δ3.97(1H,dd,5′a), δ4.25(1H,ddd,4′)δ4.3(2H,d,10),δ4.31(2H,d,12), δ4.41(1H,dd,3′)δ4.47(1H,dt,11)δ4.81 (1H,dd,2′),δ6.04(1H,d,1′),δ6.96(1H,dd,14), δ7.39-7.58(4H,m,15,16,19,20),δ7.84(1H,dd,18), δ8.29(1H,s,8),δ8.38(1H,s,2),δ8.39(1H,dd,21).

$^{13}$C NMR (CD3oD):δ52.7(t,10),δ70.9(T,5′),δ77.1(d,11), δ79.9(d,3′),δ80.1(t,12),δ82.8(d,2′),δ95.22 (d,4′),δ97.2(d,1′),δ114.3(d,14),δ129.2(d+s, 16+5),δ131.2(d,21),δ134.3(d+s,20+22),δ135.3 (d,19),δ135.7(d,15),δ136.6(d,18),δ143.3 (s,17),δ149.2(d,8),δ157.6(s,4),δ161.2(d,2), δ163.4(s,13),δ164.1(s,6).

EXAMPLE 10

N⁶-[2S-hydroxy-3-(1-naphthalenyloxy)propyl adenosine

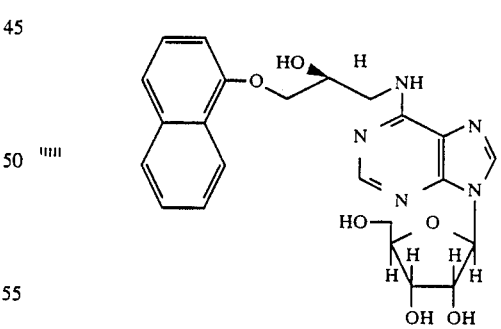

12.35 g (0.057 mole) of the product of Example 5 are dissolved in 300 mL of methanol. 7.92 mL (0.057 mole) of triethylamine and 15.43 g (0.054 mole) of the product of Example 8 are added at room temperature. The reaction mixture is heated to reflux for about 7 hours and then cooled to room temperature. The agitation is continued for minimum 1 hour. The solid is filtered, washed with 60 mL of methanol and dried under reduced pressure to afford 19.9 g of crude product.

Yield: 79%.

Purification:

The crude product (19.56 g) is dissolved in 950 mL of a mixture of methanol and water (95/5) at reflux. The solution is cooled to 10° C.<T<25° C. for about 3 hours. The solid is filtered, washed with 60 mL of methanol and dried under reduced pressure at about 80° C. to afford 15.6 g of purified product.

$[\alpha]_{579}^{24°} = -52.6°(c=1$ in DMF);DSC(MP)=139° C.

Yield: 63%.

EXAMPLE 11

N[6]-[2R-hydroxy-3-(1-naphthalenyloxy)propyl adenosine hydrochloride 9.0 ml (9 mmoles) of a 1N solution of HCl gas in anhydrous tetrahydrofuran is added to a solution of 4.68 g (10 mmoles) of the product of Example 9 in anhydrous tetrahydrofuran at 20° C. The reaction mixture is stirred at room temperature for 2 hours. The crystals of the hydrochloride salt are filtered and rinsed with 15 mL of tetrahydrofuran The compound is dried under reduced pressure at room temperature to yield 1.73 g of white powder. MP=119±2° C.(dec.)

Yield: 92.7%.

$^1$H NMR (DMSO-d6):δ3.65(2H,m),δ3.89(1H,m),δ3.99 (1H,m),δ4.20(4H,m),δ4.31(1H,m),δ4.53(1H,m), δ5.28(3 OH, massif),δ5.95(1H,d),δ7.37–7.62 (4H,m),δ7.87(1H,dd,),δ8.23–8.32(1H,d+m,), δ8.43–8.57(1H,2s),δ8.69–8.79(1H,2s),δ9.34–9.5(1H,s).

While the invention has been described and illustrated with reference to certain prepared embodiments thereof, those skilled in the art will appreciate that various changes, modifications and substitutions can be made therein without departing from the spirit and scope of the invention. For example, effective dosages other than the preferred range as set forth herein above may be applicable as a consequence of variations in the responsiveness of the mammal being treated for severity of hypertension, angina or congestive heart failure, dosage related adverse effects, if any, and analogous considerations. Likewise, the specific pharmacological responses observed may vary according to and depending upon the particular active compound selected or whether there are present certain pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow, and that such claims be interpreted as broadly as is reasonable.

What is claimed is:

1. A stereoselective method of making chiral compounds of the general formula;

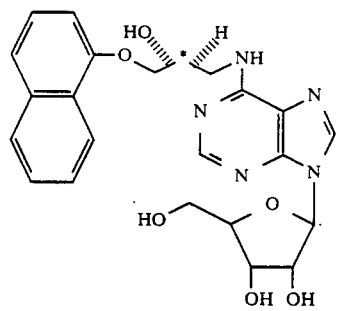

wherein * denotes the presence of a chiral carbon atom, comprising the steps of:

(a) aminating a compound of the formula;

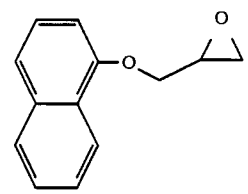

in the presence of an methanol/ammonia solution at a temperature ≦30° C. to yield a compound of the formula;

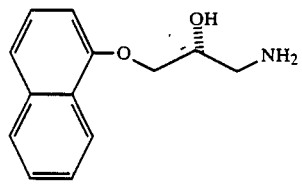

(b) reacting the product of (a) with

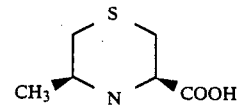

in the presence of ethanol under reflux conditions to yield, respectively, a compound of the formula;

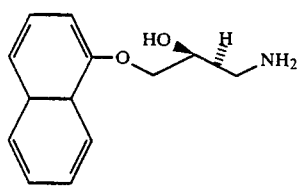

or a compound of the formula;

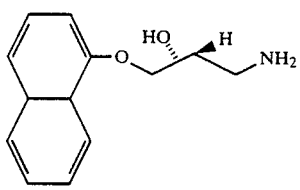

(c) reacting the desired product of (b) with a compound of the formula;

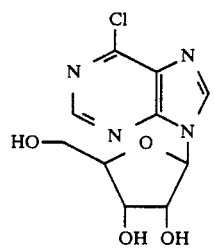

in the presence of the methanol and triethylamine under reflux conditions to yield, respectively, a compound of the formula:

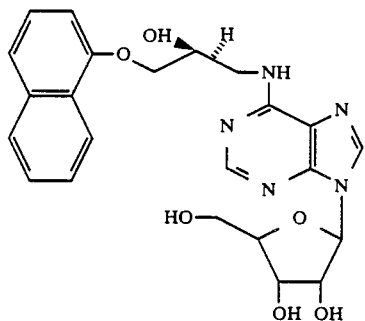

or a compound of the formula;

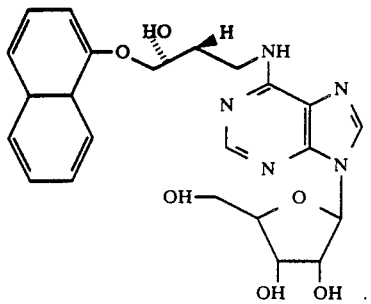

2. A method of making a compound of the structure:

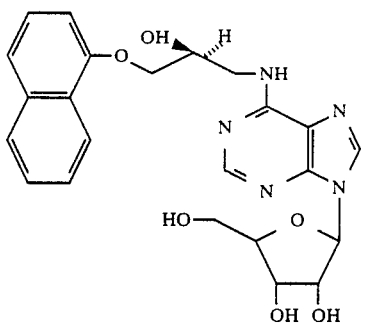

comprising the steps of:

(a) aminating a compound of the formula:

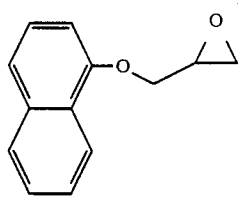

in the presence of an methanol/ammonia solution at a temperature $\leq 30°$ C. to yield a compound of the formula:

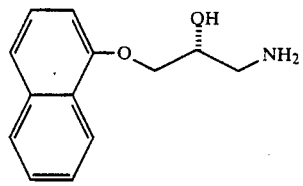

(b) and reacting the product of (a) with a compound of the formula;

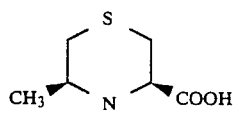

in the presence of ethanol under reflux conditions to yield a compound of the formula:

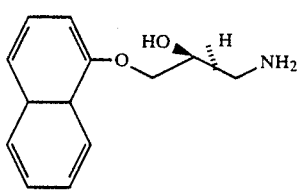

(c) reacting the desired product of (b) with a compound of the formula:

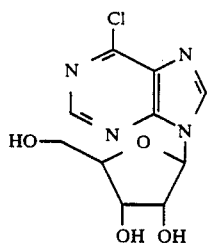

in the presence of methanol and triethylamine under reflux conditions to yield a compound of the formula

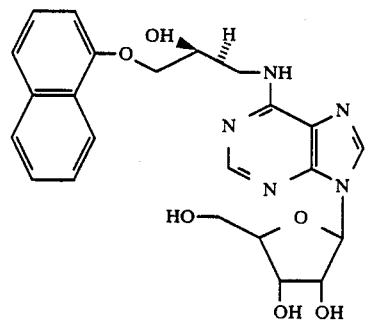

3. A method of making a compound of the structure:

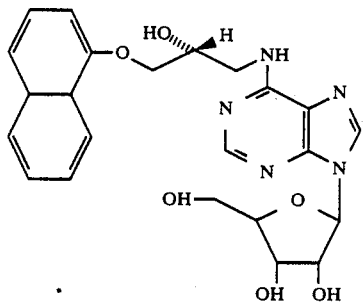

comprising the steps of:

(a) aminating a compound of the formula:

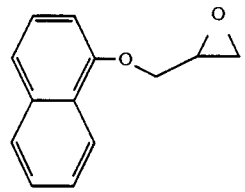

in the presence of an methanol/ammonia solution at temperature $\leq 30°$ C. to yield a compound of the formula:

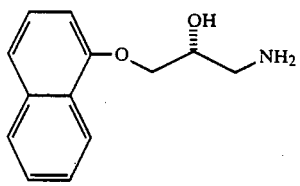

(b) and reacting the product of (a) with a compound of the formula:

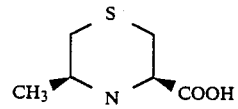

in the presence of ethanol under reflux conditions
(c) reacting the product of (b) with a compound of the formula

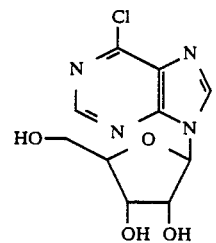

in the presence of methanol and triethylamine under reflux conditions to yield a compound of the formula

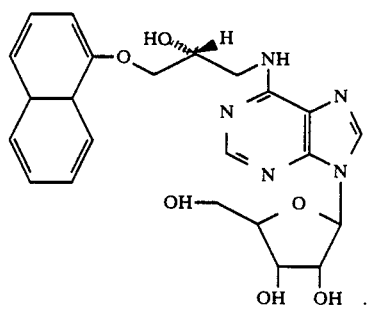

* * * * *

UNITED STATES PATENT AND TRADEMARK OFFICE
CERTIFICATE OF CORRECTION

PATENT NO. : 4,992,535
DATED : Feb. 12, 1991
INVENTOR(S) : Libert, et. al.

It is certified that error appears in the above-identified patent and that said Letters Patent is hereby corrected as shown below:

Column 1, line 42, reading "including the brain Renin, which" should read -- including the brain. Renin, which --.

Column 2, line 15, represented by the formula reading

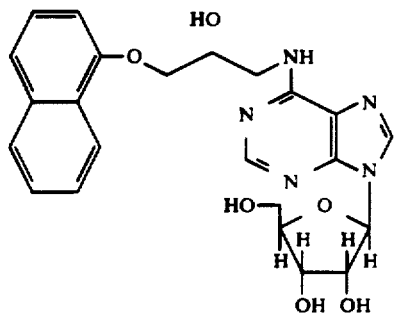   should read   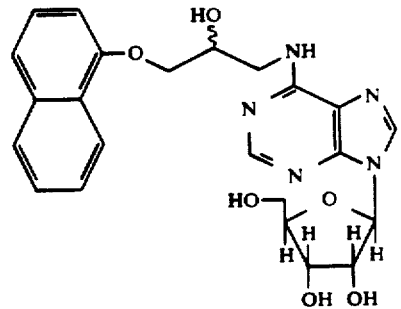

Column 2, line 40, the formula reading

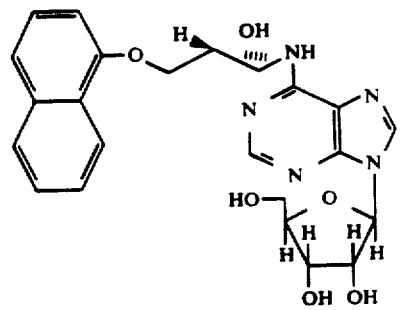   should read   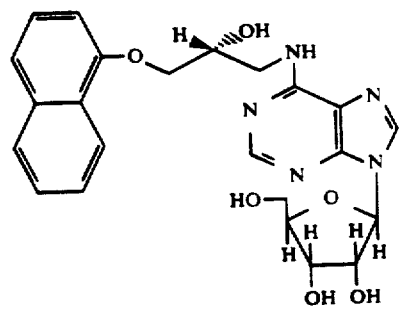

UNITED STATES PATENT AND TRADEMARK OFFICE
CERTIFICATE OF CORRECTION

PATENT NO. : 4,992,535
DATED : Feb. 12, 1991
INVENTOR(S) : Libert, et. al.

It is certified that error appears in the above-identified patent and that said Letters Patent is hereby corrected as shown below:

Column 2, line 55, the formula reading

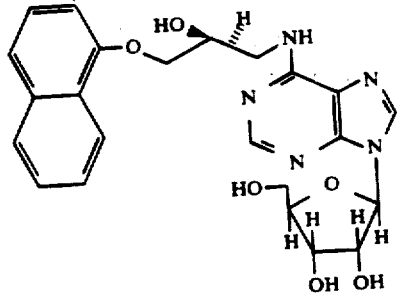     should read     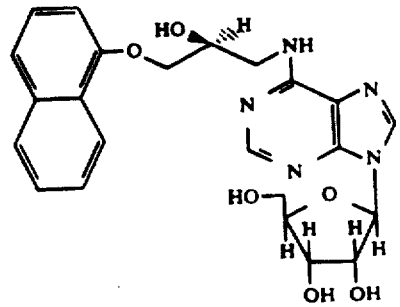

Column 4, line 8, the formula reading

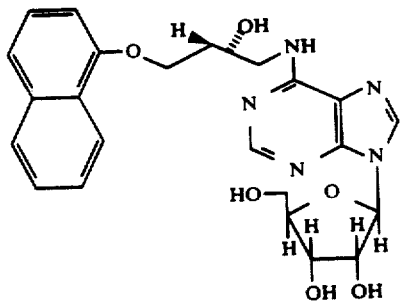     should read     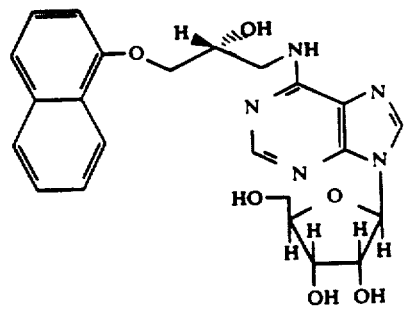

Column 4, line 26, the formula reading

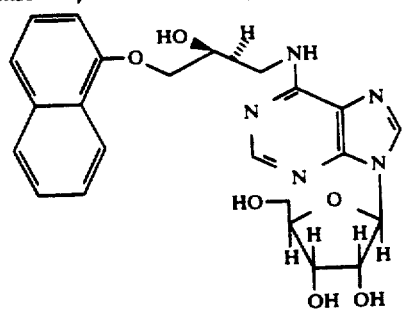     should read     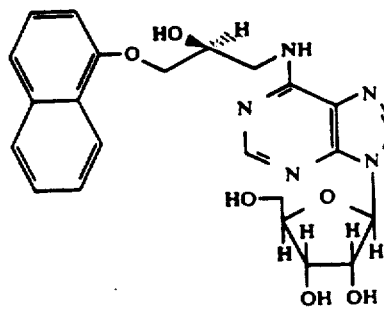

UNITED STATES PATENT AND TRADEMARK OFFICE
CERTIFICATE OF CORRECTION

PATENT NO. : 4,992,535          Page 3 of 14

DATED : Feb. 12, 1991

INVENTOR(S) : Libert, et. al.

It is certified that error appears in the above-identified patent and that said Letters Patent is hereby corrected as shown below:

Column 5,6 Scheme I reading

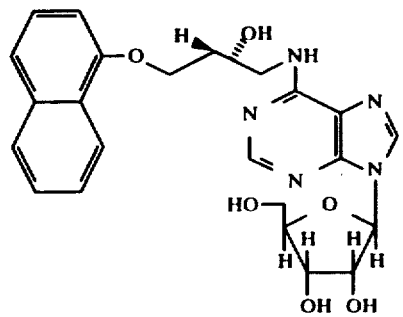

should read

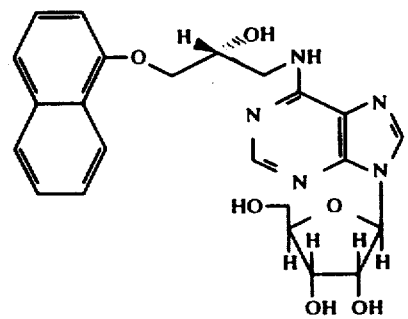

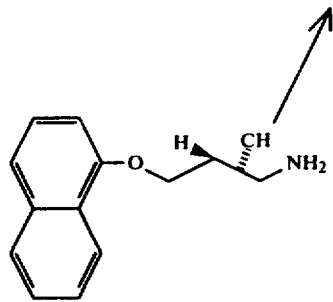

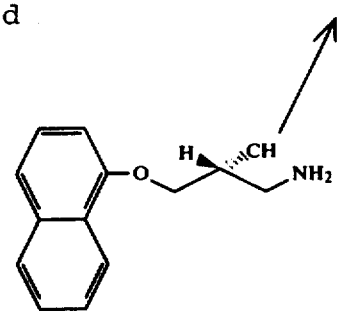

UNITED STATES PATENT AND TRADEMARK OFFICE
CERTIFICATE OF CORRECTION

PATENT NO. : 4,992,535

DATED : Feb. 12, 1991

INVENTOR(S) : Libert, et. al.

It is certified that error appears in the above-identified patent and that said Letters Patent is hereby corrected as shown below:

Column 5,6 Scheme I, continued, reading

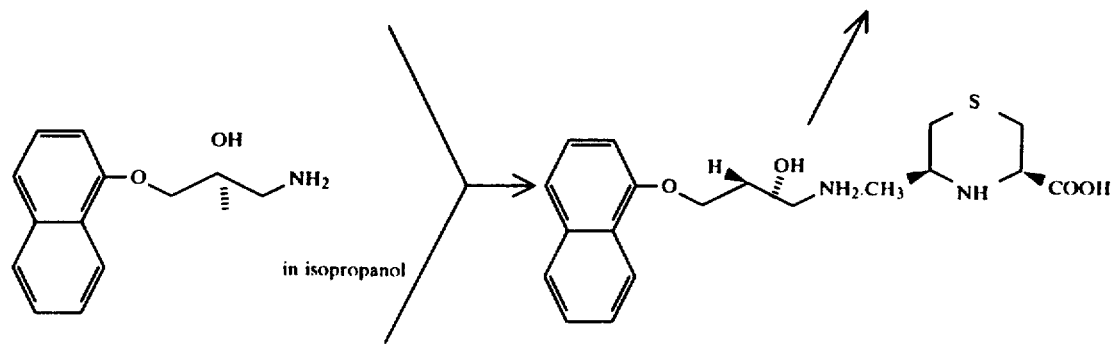

should read

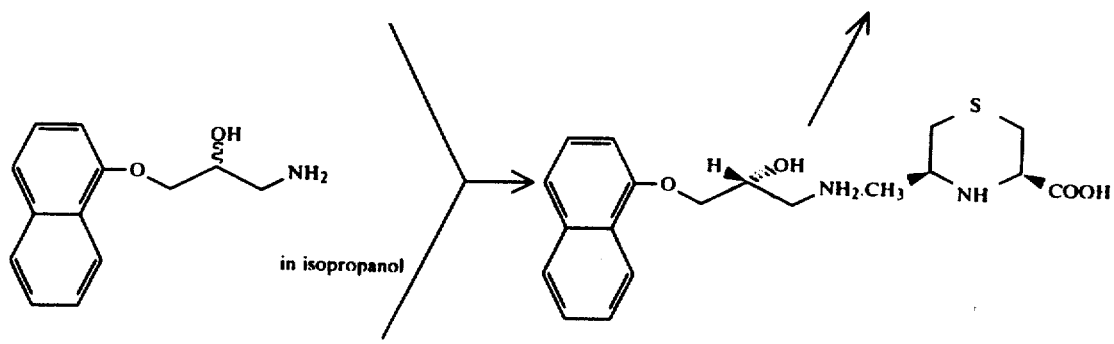

UNITED STATES PATENT AND TRADEMARK OFFICE
CERTIFICATE OF CORRECTION

PATENT NO. : 4,992,535

DATED : Feb. 12, 1991

INVENTOR(S) : Libert, et. al.

It is certified that error appears in the above-identified patent and that said Letters Patent is hereby corrected as shown below:

Column 7,8, Scheme 2, reading

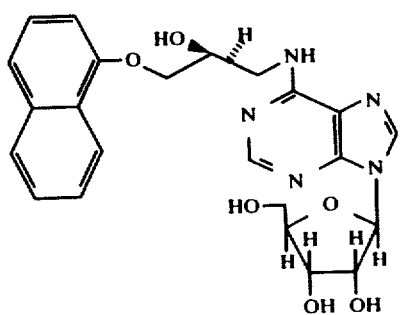

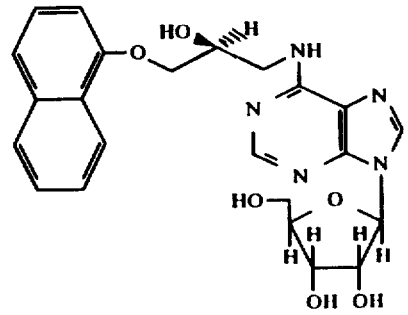

should read

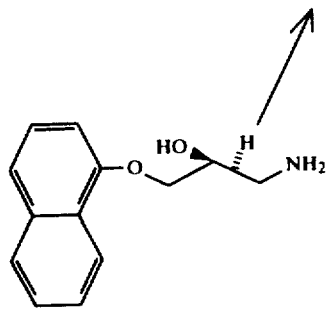

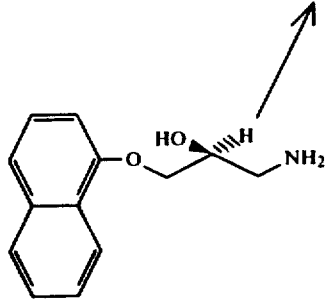

UNITED STATES PATENT AND TRADEMARK OFFICE
CERTIFICATE OF CORRECTION

PATENT NO. : 4,992,535

DATED : Feb. 12, 1991

INVENTOR(S) : Libert, et. al.

It is certified that error appears in the above-identified patent and that said Letters Patent is hereby corrected as shown below:

Column 7,8, Scheme 2 continued, reading

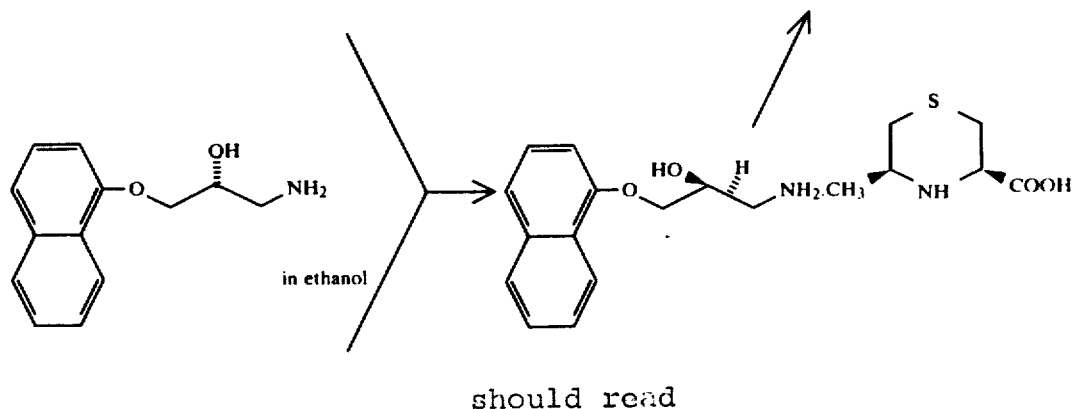

should read

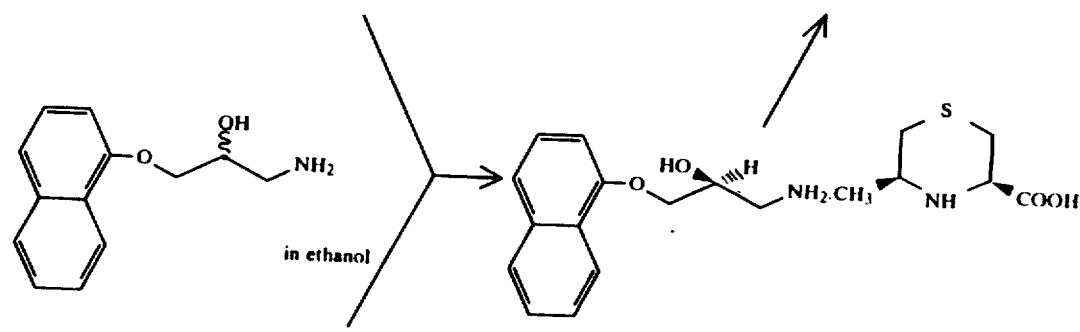

UNITED STATES PATENT AND TRADEMARK OFFICE
CERTIFICATE OF CORRECTION

PATENT NO. : 4,992,535
DATED : Feb. 12, 1991
INVENTOR(S) : Libert, et. al.

It is certified that error appears in the above-identified patent and that said Letters Patent is hereby corrected as shown below:

Column 9, line 7 reading

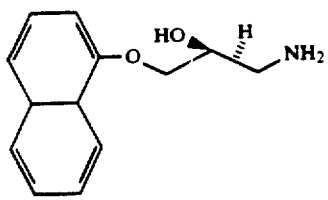 should read 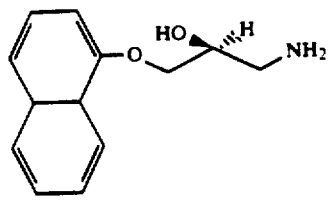

Column 9, line 20 reading

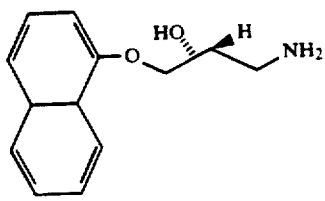 should read 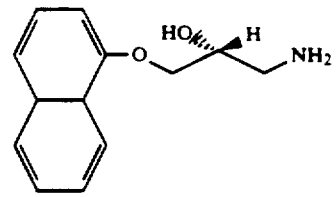

Column 10, line 20, reading "beta lactose" should read -- beta-lactose --.

Column 10, line 32, reading "rennin release" should read -- renin-release --.

Column 12, line 49, reading "=different from vehicle" should read -- + = different from vehicle --.

Column 12, line 53, reading "above pre treatment" should read -- above pre-treatment --.

Column 14, line 21, reading "28 9 Kg" should read -- 28.9 Kg --.

UNITED STATES PATENT AND TRADEMARK OFFICE
CERTIFICATE OF CORRECTION

PATENT NO. : 4,992,535
DATED : Feb. 12, 1991
INVENTOR(S) : Libert, et. al.

It is certified that error appears in the above-identified patent and that said Letters Patent is hereby corrected as shown below:

Column 14, line 49, reading "9 Kg(61.B" should read -- 9 Kg(61.8 --.

Column 14, lines 60-61, reading "$^1$H    NMR(CDCL$_3$):" should read -- $^1$H NMR(CDCL$_3$): --.

Column 15, line 5, reading

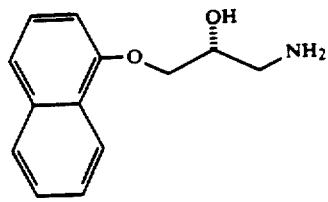   should read   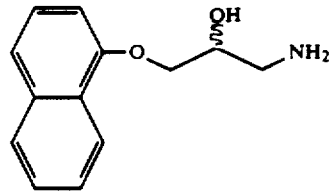

Column 15, line 13, reading "116 L Of" should read -- 116 L of --.

Column 16, line 6, reading "pH=5,6)" should read -- pH≡5,6) --.

Column 16, line 37, reading "to afford 558 of product" should read -- to afford 558g of product --.

Column 17, lines 13-14, reading "$^1$H    NMR    (DSMO-d6);" should read -- $^1$H NMR(DSMO-d6); --.

Column 17, line 23, reading

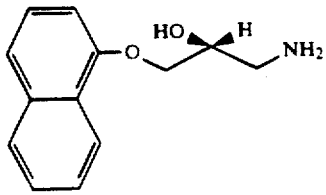   should read   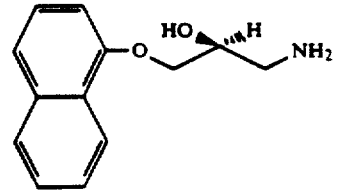

UNITED STATES PATENT AND TRADEMARK OFFICE
CERTIFICATE OF CORRECTION

PATENT NO. : 4,992,535

DATED : Feb. 12, 1991

INVENTOR(S) : Libert, et. al.

It is certified that error appears in the above-identified patent and that said Letters Patent is hereby corrected as shown below:

Column 18, line 17, reading "$^{13}C$ NMR (DSMOd-6);" should read -- $^{13}C$ NMR (DSMOd-6); --.

Column 18, line 64, reading "$^{13}C$ NMR (CDCL3):" should read -- $^{13}C$ NMR (CDCL3): --.

Column 19, lines 33-34, reading "$^{1}H$ NMR (DSMO-d6):" should read -- $^{1}H$ NMR (DSMO-d6): --.

Column 19, line 49, reading

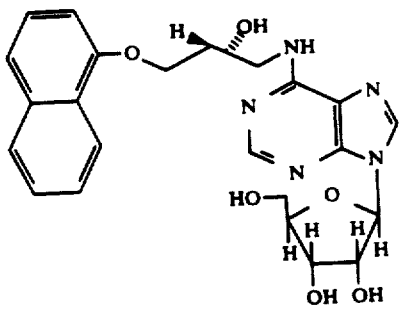   should read   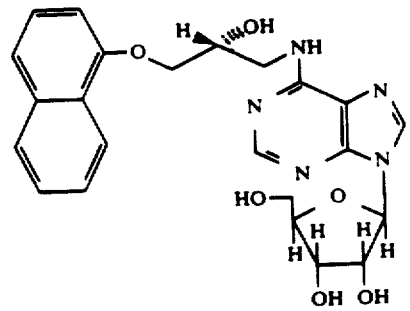

Column 20, lines 21-22, reading "$[\alpha]_{579}^{25°}$ C=44.8°(c=0.5 in DMF);" should read -- $[\alpha]_{579}^{25°}$ c=44.8°(c=0.5 in DMF); --.

Column 20, lines 32-33, reading "$^{13}C$ NMR (CD3oD):" should read -- $^{13}C$ NMR (CD3OD): --.

UNITED STATES PATENT AND TRADEMARK OFFICE
CERTIFICATE OF CORRECTION

PATENT NO. : 4,992,535
DATED : Feb. 12, 1991
INVENTOR(S) : Libert, et. al.

It is certified that error appears in the above-identified patent and that said Letters Patent is hereby corrected as shown below:

Column 20, line 45, reading

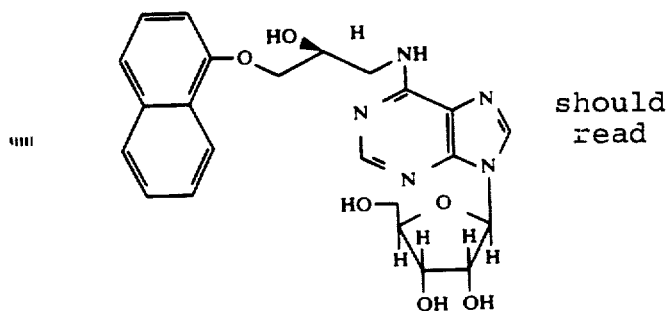   should read   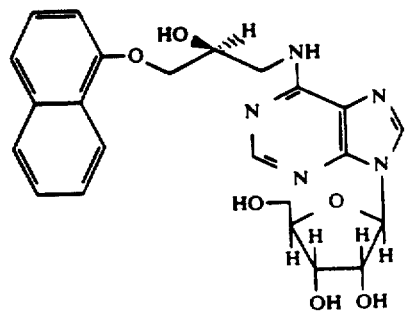

Column 21, lines 8-9, reading "[60]$_{579}^{24°}$ C=-52.6°(c=1 in DMF);DSC(MP" should read -- [60]$_{579}^{24}$ C=-52.6°(c=1 inDMF);DSC(MP --.

Column 21, line 30-31, reading "$^1$H NMR (DMSO-d6);" should read -- $^1$H NMR (DMSO-d6); --.

Column 22, line 5, the structure reading

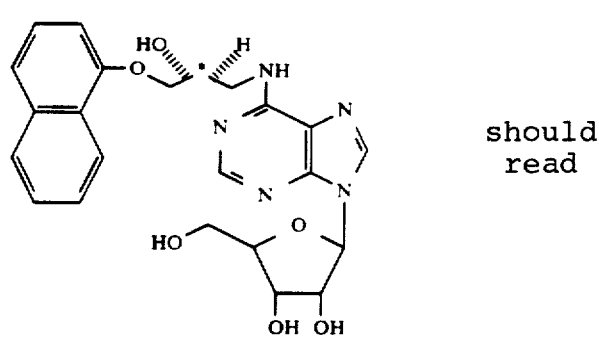   should read   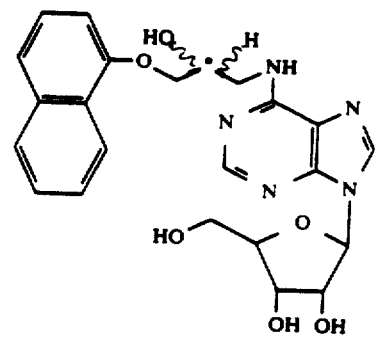

UNITED STATES PATENT AND TRADEMARK OFFICE
CERTIFICATE OF CORRECTION

PATENT NO. : 4,992,535

DATED : Feb. 12, 1991

INVENTOR(S) : Libert, et. al.

It is certified that error appears in the above-identified patent and that said Letters Patent is hereby corrected as shown below:

Column 22, line 37, structure reading

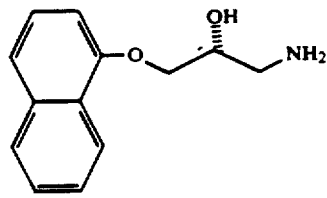   should read   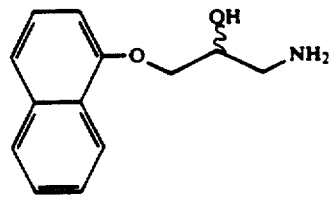

Column 22, line 60, structure reading

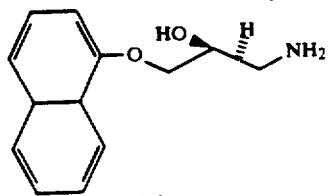   should read   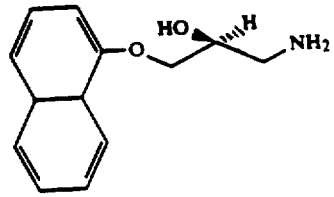

Column 23, line 5, structure reading

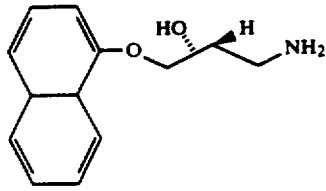   should read   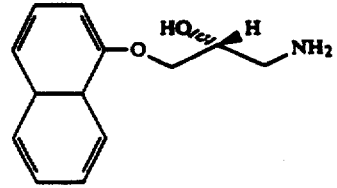

UNITED STATES PATENT AND TRADEMARK OFFICE
CERTIFICATE OF CORRECTION

PATENT NO. : 4,992,535
DATED : Feb. 12, 1991
INVENTOR(S) : Libert, et. al.

It is certified that error appears in the above-identified patent and that said Letters Patent is hereby corrected as shown below:

Column 23, line 35, structure reading

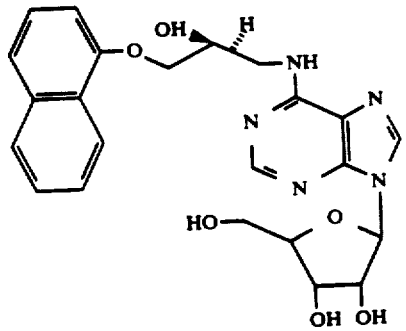      should read      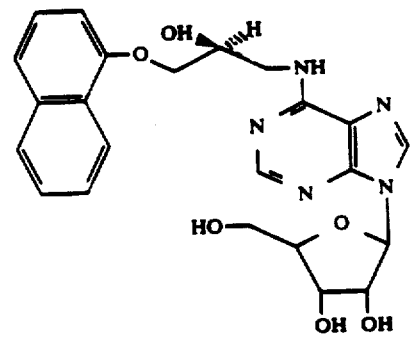

Column 23, line 54, structure reading

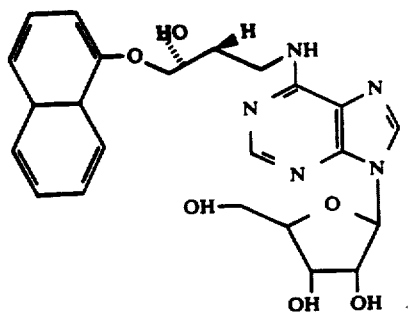      should read      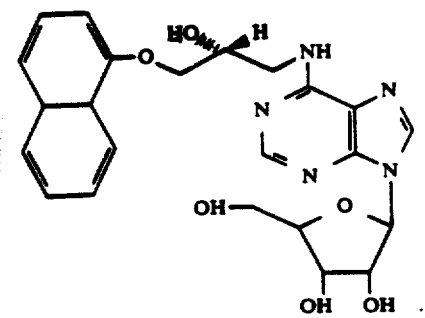

UNITED STATES PATENT AND TRADEMARK OFFICE
CERTIFICATE OF CORRECTION

PATENT NO. : 4,922,535
DATED : Feb. 12, 1991
INVENTOR(S) : Libert, et. al.

It is certified that error appears in the above-identified patent and that said Letters Patent is hereby corrected as shown below:

Column 24, line 5, structure reading

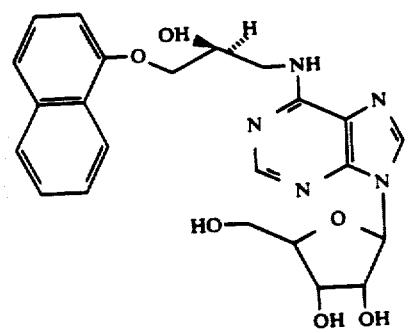     should read     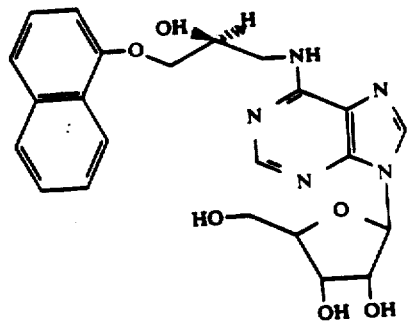

Column 24, line 37, structure reading

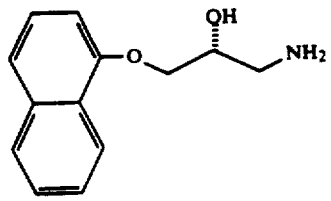     should read     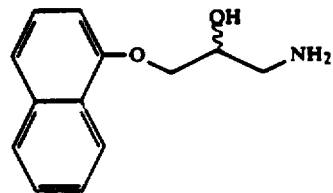

Column 24, line 60, structure reading

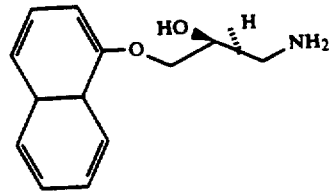     should read     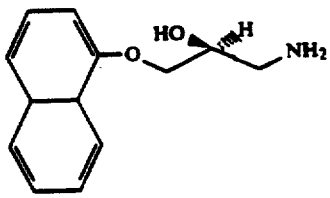

UNITED STATES PATENT AND TRADEMARK OFFICE
CERTIFICATE OF CORRECTION

PATENT NO. : 4,992,535

DATED : Feb. 12, 1991

INVENTOR(S) : Libert, et. al.

It is certified that error appears in the above-identified patent and that said Letters Patent is hereby corrected as shown below:

Column 25, line 27, structure reading

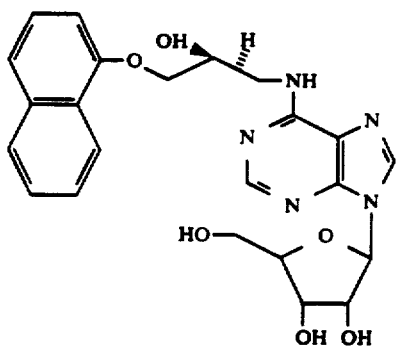 should read 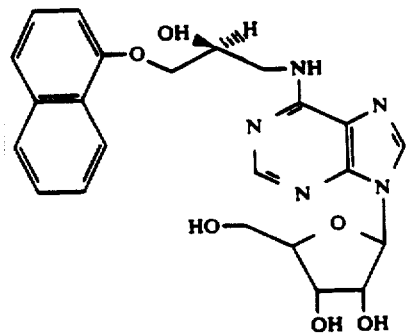

Signed and Sealed this

Fifteenth Day of December, 1992

Attest:

DOUGLAS B. COMER

Attesting Officer

Acting Commissioner of Patents and Trademarks